(12) United States Patent
Kugler et al.

(10) Patent No.: US 7,766,917 B2
(45) Date of Patent: Aug. 3, 2010

(54) EXTRACTOR FOR A BONE CONNECTION ELEMENT

(75) Inventors: Stefan Kugler, Bern (CH); André Gasser, Langendorf (CH); Christian Lutz, Mönkeberg (DE)

(73) Assignee: Stryker Trauma SA (CH)

( * ) Notice: Subject to any disclaimer, the term of this patent is extended or adjusted under 35 U.S.C. 154(b) by 457 days.

(21) Appl. No.: 11/975,846

(22) Filed: Oct. 22, 2007

(65) Prior Publication Data

US 2008/0045969 A1 Feb. 21, 2008

Related U.S. Application Data

(63) Continuation of application No. 10/999,668, filed on Nov. 30, 2004, now abandoned.

(51) Int. Cl.
*A61B 17/58* (2006.01)
(52) U.S. Cl. ........................ 606/86 R; 29/275
(58) Field of Classification Search ............... 606/86 R, 606/99, 104; 81/53.2, 451, 452, 458, 465; 29/255, 275, 278
See application file for complete search history.

(56) References Cited

U.S. PATENT DOCUMENTS

| | | | |
|---|---|---|---|
| 1,007,107 A | 10/1911 | Hulsmann | |
| 2,068,021 A | 1/1937 | Hamman | |
| 2,243,717 A | 5/1941 | Moreira | |
| 2,550,866 A | 5/1951 | Rosan | |
| 2,562,419 A | 7/1951 | Ferris | |
| 2,631,584 A | 3/1953 | Purificato | |
| 4,877,020 A | 10/1989 | Vich et al. | |
| 5,269,784 A | 12/1993 | Mast | |
| 5,885,299 A | 3/1999 | Winslow et al. | |
| 5,954,722 A | 9/1999 | Bono | |
| 5,976,141 A | 11/1999 | Haag et al. | |
| 6,077,267 A | 6/2000 | Huene | |
| 6,112,623 A | 9/2000 | Bigand et al. | |
| 6,235,033 B1 | 5/2001 | Brace et al. | |
| 6,258,090 B1 | 7/2001 | Jackson | |
| 7,115,128 B2 | 10/2006 | Michelson | |
| 2002/0045901 A1 | 4/2002 | Wagner et al. | |
| 2002/0099386 A1 | 7/2002 | Beger et al. | |
| 2004/0254579 A1 | 12/2004 | Buhren et al. | |

FOREIGN PATENT DOCUMENTS

| DE | 198 41 252 A1 | 3/2000 |
|---|---|---|
| JP | 2003-265492 | 9/2003 |

*Primary Examiner*—Thomas C Barrett
*Assistant Examiner*—Nicholas Woodall
(74) *Attorney, Agent, or Firm*—Lerner, David, Littenberg, Krumholz & Mentlik, LLP

(57) ABSTRACT

An extractor is provided to extract an insert used with a bone connection element such as a bone plate having at least one opening for a bone screw used with the insert. The extractor has an outer hollow sleeve having proximal abutment surface for engaging a surface portion of the bone plate, and an inner bar having a diameter enabling the insertion of the bar into the hollow sleeve. The bar has a threaded leading end to engage the thread of the insert to be extracted. The hollow sleeve has an inner thread and the inner bar has an outer threaded element for engaging the inner thread of the hollow sleeve. The outer threaded element is positioned with respect to the bar in a longitudinal position to enable the threaded locking end to extend beyond the proximal abutment surface of the sleeve to be threaded into the insert.

14 Claims, 5 Drawing Sheets

EXTRACTOR FOR A BONE CONNECTION ELEMENT

CROSS-REFERENCE TO RELATED APPLICATIONS

This application is a continuation of U.S. application Ser. No. 10/999,668, filed on Nov. 30, 2004, the disclosure of which is incorporated herein by reference.

BACKGROUND OF THE INVENTION

The invention concerns an extractor device for an insert to be used with a bone connection element usable within an implantable orthopedic device having a load-bearing element such as a bone plate with at least one opening for a fixation element such as a bone screw. A screw can be used such as shown in the application entitled "Self-Guiding Threaded Fastener" with inventor Yves Crozet filed on Nov. 30, 2004 the entire disclosure of which is incorporated herein by reference. The invention is furthermore related to the insert itself and to an insertion device for such an insert. The inserts may be used in bone plating systems such as described in the application entitled "Bone Plating Implants, Instruments and Methods" filed Nov. 30, 2004 listing Yves Crozet, Christian Lutz and Renee Wirth as inventors the disclosure of which is hereby incorporated by reference.

Such an insert is provided that can be inserted into the opening in a receptacle in which the external shape of the insert is at least partially complementary to the internal shape of the receptacle. The insert has a central through-bore for mounting a body of the fixation element. The implantable orthopedic device has a structure for holding the insert in the receptacle.

A series of implantable orthopedic devices with load-bearing elements, such as bone plates, with openings for the insertion of fixation elements in such load-bearers are known from the prior art. Among them are proposals for the monoaxial as well as poly-axial attachment of fixation elements, particularly screws.

As an example for a device of this type having poly-axial attachment of screws in load-bearing elements is shown in U.S. Pat. No. 5,954,722. Other bone plates with inserts are shown in U.S. Pat. Nos. 5,269,784, 5,976,141 and 5,607,428. One advantageous insert is shown in WO 2004/082493, which is hereby incorporated by reference.

FIG. 1 OF WO 2004/082493 shows a perspective view of an insert to be used with a load-bearing element such as a bone plate. FIG. 2 is a sectional side view of a load-bearing element with another insert inserted. The load-bearing elements can be equipped in advance with standard inserts. This enables an easier more cost efficient production of bone plates giving the surgeon the possibility to adapt the bone plate according to his needs. A surgeon thus may turn an opening in a bone plate adapted to receive a non-locking screw to an aperture in which a locking screw having a threaded portion adapted to threadably engage the plate via the insert can be used. Then it may sometimes be necessary to extract one or the other insert and to replace it by another different insert or to leave the bore or opening empty. The prior art exhibits the disadvantage that there are no extracting tools provided to help the surgeon team to extract inserts.

SUMMARY OF THE INVENTION

It is therefore one aspect of the invention to provide an extractor device allowing to extract easily different inserts from different load-bearing elements.

This aspect is fulfilled according to the invention for an extractor device of the aforementioned type which can easily remove an insert from a bone plate opening so that it may receive a non-locking screw.

This object is achieved by an extractor device, which can engage the insert in a manner that enables the extraction of the said insert from the load-bearing element in a simple and swift movement. The extraction can be accomplished for quite a number of different inserts, with different angled positions. Of particular advantage is that the secure extraction of the insert can be assured directly and automatically with the use of the extractor device.

One single extractor device is sufficient to provide the necessary help to extract various inserts with inclined axes as long as the inner bore has a predefined thread. The surgeon can therefore use a bone plate with inserts with predefined angles for the insertion of poly- or monoaxial screws and change one or more of the inserts to orient bone screws at a number of different defined angles in a simple manner.

It is another aspect of the invention to provide an insert, which is easy to handle for the surgeon.

It is furthermore an aspect of the invention to provide an insertion device allowing a simple insertion of different inserts into different load-bearing elements.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
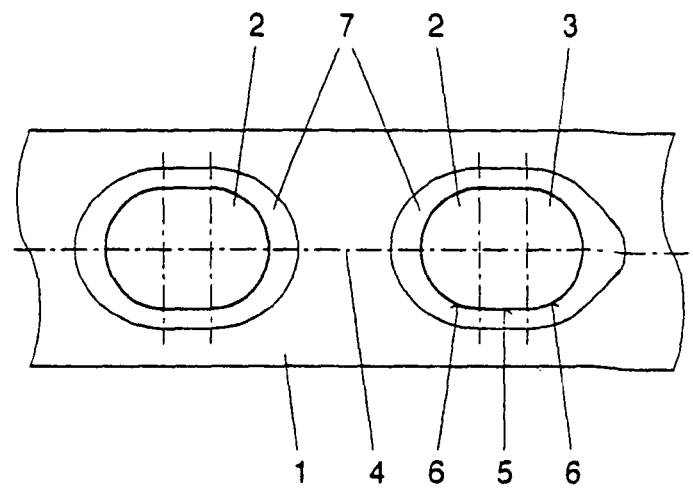
FIG. 1 is a top view of a load-bearing element in the form of a bone plate with a row of attachment bores.
Figure 2:
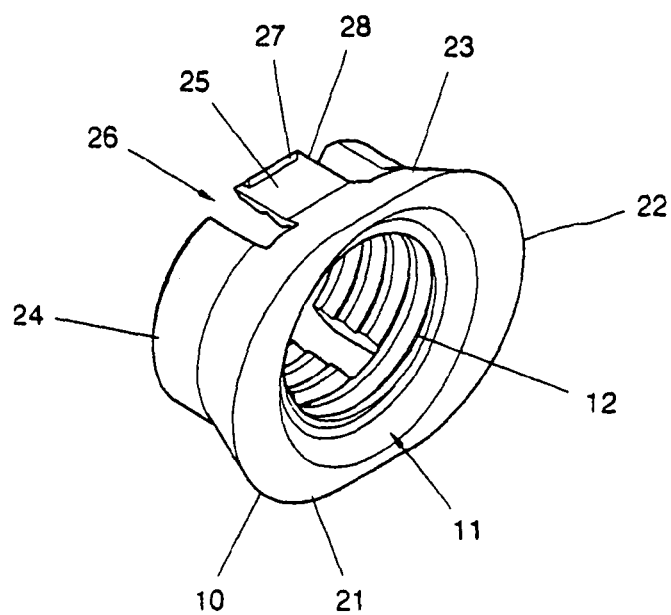
FIG. 2 is a perspective view of a first insert to be used with a load-bearing element.
Figure 3:
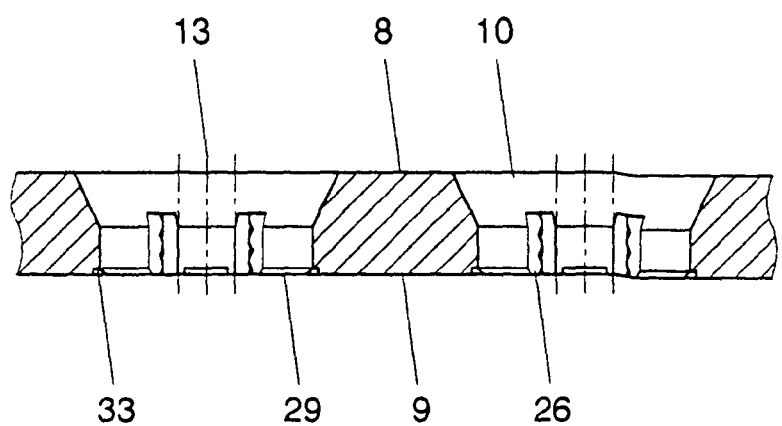
FIG. 3 is a sectional side view of a load-bearing element with a second insert inserted.

Referring to FIG. 1 there is shown a top view of a load-bearing element in the form of a plate or load bearing element 1 with a row of attachment bores 2 arranged along the longitudinal direction of plate 1. FIG. 2 shows a perspective view of a first insert 10 to be used with load-bearing element 1. Bores 2 of plate 1 are through-bores that exhibit an oval central opening 3. At opening 3 there are two sidewalls 5 on opposite sides of axis 4, which extend parallel to the direction of longitudinal axis 4 of plate 1 and extend at right angles to the surfaces of the plate. These parallel sidewalls 5 are connected on both ends by semicircular walls 6, each forming a semi-cylindrical boundary so that together the aforementioned oval opening 3 results.

In other forms of the plate, oval bores 2 can also be provided. Bores 2 can also be elliptical or of a common elongated form. What is essential is the multiplicity of functions for the selection of attachment elements or fasteners made possible by insert 10 shown in FIG. 2. Through the mostly elongated form of plate 1, elongated bores 2 are preferred over circular bores in order to maintain flexibility with the insertion of screws with larger diameters. The bore may also be essentially cylindrical with the disadvantage that the insert 10 has less material for providing inclined holes in the insert 10.

Arranged around the cylindrical, not necessarily circular walls 5, 6 forming opening 3 is chamfered surface area 7, extending and tapering inwardly from the upper surface 8 of plate 1 that faces away from the bone during implantation. The form of this area 7 is preferably part-spherical.

The top surface 8 of load-bearing element 1 is formed somewhat deeper in the side area 13 near bores 2. The same is true for upper edge of sidewall 5, which are shown to be lower (closer to the plate bottom surface) in a direction opposite the bore ends in the longitudinal direction of longitudinal axis 4. Bottom surface 9, which is closest to the bone in insertion during surgery is here locally flat. Normally, plates 1 can exhibit continuous surfaces 8 and undersurfaces 9 which at each point, for the function of positioning on the bone can always be considered to be flat. But here too, positioning on curved or bent surfaces can be provided.

FIG. 2 shows a perspective view of an insert 10 to be used with a load-bearing element 1 according to FIG. 1. Similar characteristics appear in all figures with the same reference numerals. Each insert 10 is designed to be shaped complementary to bore 2 for locking therein with respect to areas 7 and sidewalls 5. Insert 10 has a central bore 11 with an internal threading 12. Internal threading 12 can be cylindrical or slightly conical. Insert 10 can have an area that extends beyond lower surface 9 of plate 1 that is adjacent the bone. In particular, insert 10 has locking mechanisms along its edges. In particular, the locking mechanism can be two projecting rims that engage the underside 9 of plate 1 after the insertion of insert 10. The insert 10, when it is inserted into plate 1, with its extension area, can form a distance spacer with regard to the bone material into which a screw that has been inserted into bore 11 is turned.

It is also possible that, at least along the length of the longitudinal axis 4 of the load-bearing element 1, a recess 33 is provided on the bottom surface 9 around opening 2 of the plate 1. This recess can also be provided on the narrow side. In addition, insert 10 is provided with a projecting rim 27 that is arranged in such a way that the bottom of insert 10 does not project beyond lower surface 9. The underside of insert 10 is thus at least flush with the aforementioned surface 9 of the load-bearing element 1.

The reference numeral 21 refers to the surface of insert 10 having a circumference 22 that meets with the edge of area 8 of plate 1. A spherical surface 23 extends downwardly from surface 21 and is shaped so as to have complementary surface contact with surface 7. Semicircular extension 24 extends downwardly from surface 23 and is in conforming contact, without any significant play, with area 6 of bore 2.

Figure 13:
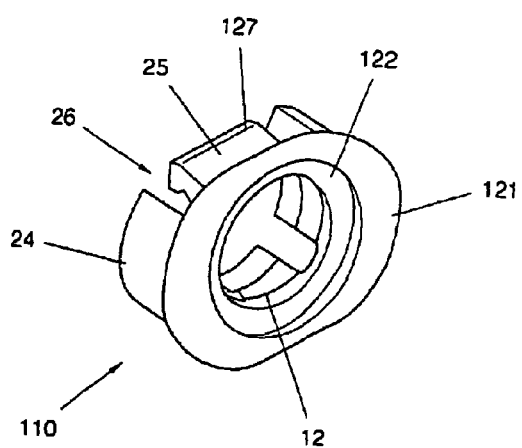
FIG. 13 is a perspective view of a second insert to be used with a load-bearing element.
Figure 14:
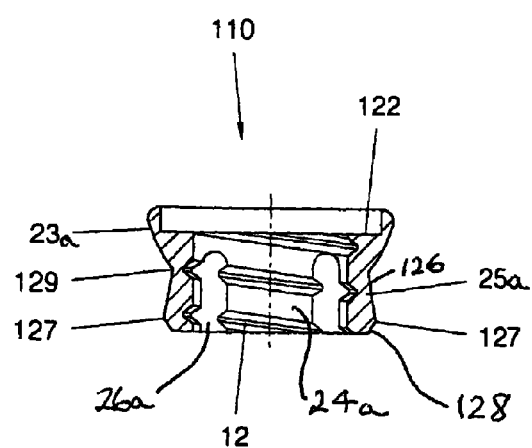
FIG. 14 is a sectional side view of the insert according to FIG. 13.
Figure 15:
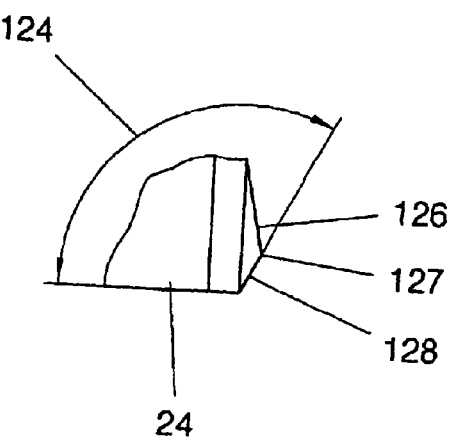
FIG. 15 is an enlarged side view showing a detail of the insert according to FIG. 13.

The area lying opposite the longitudinal surface 5 consists of a resilient extension 25 on each side, in which, in the preferred embodiment shown, each extension 25 is provided with slots 26. Each extension 25 has, on its lower edge, a projecting rim 27 facing outward from the point of view of the insert with an upward-facing shoulder 28 with an outer edge 29. The surface of rim 27 that is facing toward the bone can be inclined. Extension 25 is also to a certain extent, flexible. In inserting insert 10, extension 25 then slides into bore 2 and is deflected inwardly by the projecting rim 27. Once insert 10 is completely inserted, shoulder 28 slides against underside 9 of plate 1 and locks insert 10 in plate 1. This locking is additionally ensured by the subsequent insertion of a bone screw (not shown). FIGS. 13 thru 15 show a slightly modified insert having tapered side elements or sidewalls 25a which taper inwardly from their free edges 127 to surface 23a. The insert will be described in more detail below.

It is one aspect of the invention to provide an extractor device being able to extract such a fixed insert 10 from the plate 1. Pressure has to be exerted in such a way that an inward deflection of extension 25, 25a is obtained so that projecting rim 27, 127 is no longer secured under plate 1 or in a recess provided at the bottom of the plate 1. It should be noted that the extractor device has to also function if extension 25, and with it projecting rim 27, are not arranged as two extensions 25 on the opposing longer sides of insert 10. The design can also include resilient extensions on the narrow sides of an insert, i.e. corresponding to the location of the semicircular cylindrical extensions 24. Extensions 25 can also be arranged in an alternating manner. There can also be only one or two more extensions.

Figure 4:
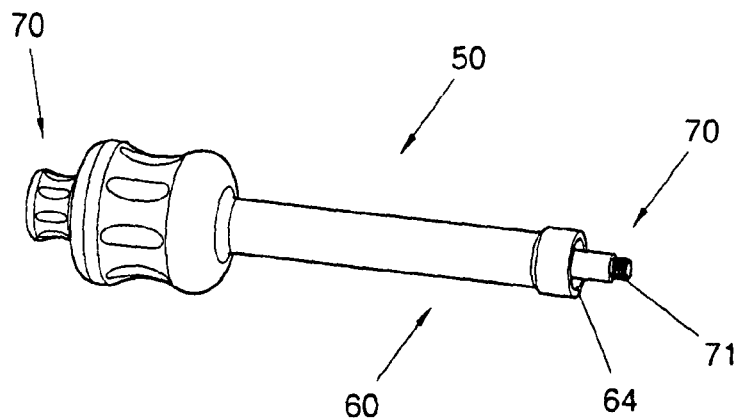
FIG. 4 is a perspective view of an extractor device according to one embodiment of the invention.

Referring to FIG. 4 there is shown a perspective view of an extractor device 50 according to a preferred embodiment of the invention. Extractor device 50 comprises two different parts, an outer sleeve 60 and an inner bar 70 extending on both sides beyond the through going bore or cannulation inside the sleeve 60. The outer sleeve 60 is shown in greater detail in FIG. 6, the inner bar 70 is shown in greater detail in FIG. 7 to 9.

Figure 5:
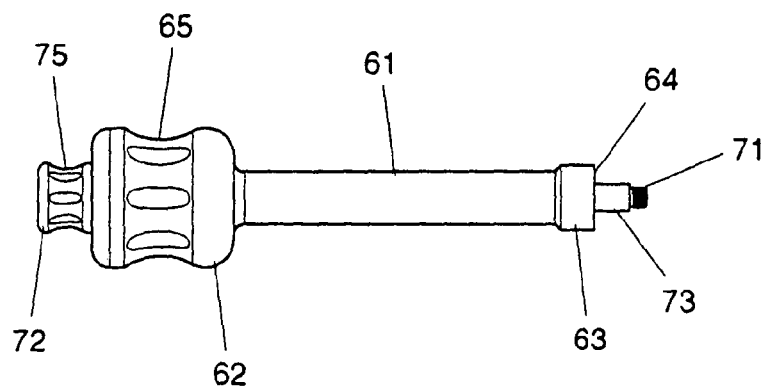
FIG. 5 is a side view of the device according to FIG. 4.

FIG. 5 shows a side view of the device 50 according to FIG. 4. The outer sleeve 60 comprises a hollow sleeve part 61 having a first handle part 62 being an integral part of the sleeve 60. The first handle part 62 comprises a circumferential depression 65 to provide a grip portion for the hand of a user of the device 50. A thickened abutment sleeve 63 is provided on the opposite end of the hollow sleeve part 61 ending in a round abutment ring 64 having a larger diameter than the diameter of the proximal bar section 73 of the inner bar 70. The function of the abutment ring 64 will be explained below. The length of the external sleeve 60 can be between 150 and 200 millimeter with a first handle part 62 diameter of 30 to 50 millimeter and a outer sleeve diameter of e.g. 14 millimeter.

It can be seen from both, FIGS. 4 and 5 that the preferred inner bar 70 extends beyond both ends of outer sleeve 60. On the side of the first handle part 62 the inner bar 70 comprises a second handle part 72 having a circumferential gripping depression 75. The radius of the second handle part 72 is greater than the inner diameter of the hollow sleeve 60. An engagement thread 71 is provided at the end of the proximal bar section 73 extending beyond the hollow sleeve 60.

Figure 6:
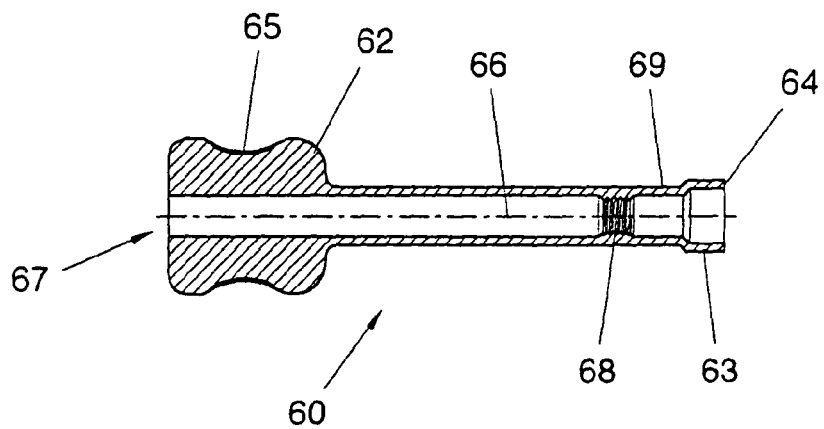
FIG. 6 is a sectional side view of the external sleeve of the extractor device according to FIG. 4.

FIG. 6 shows a sectional side view of the preferred external sleeve 60 of extractor device 50 according to FIG. 4. The hollow sleeve comprises a through-bore extending along axis 82a with a middle section 66 having a first diameter and extending from the opening 67 at the distal end near the first handle part 62 towards an internal thread 68. The through-bore comprises on its proximal end 69 a second diameter being smaller than the above-mentioned first inner diameter. The internal thread 68 can have a length of e.g. 10 millimeter with 5 to 10 full threads. The internal thread 68 is positioned near the proximal end of the sleeve 60, e.g. between 20 and 40 millimeter from the abutment ring 64. It would also be possible to locate the internal thread 68 near or under the first handle part 62.

The first inner diameter, being the inner diameter of a part of the sleeve 60, can be chosen to be 12 Millimeter, said second diameter of the end portion 69 can be chosen to be 11 millimeter. The enlarged section 63 can have a diameter of 14 millimeter.

Figure 7:
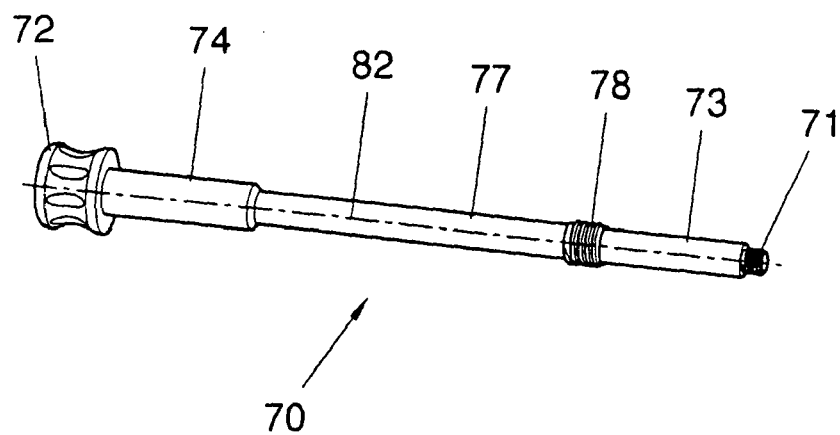
FIG. 7 is a perspective view of the inner bar of the extractor device according to FIG. 4.
Figure 8:
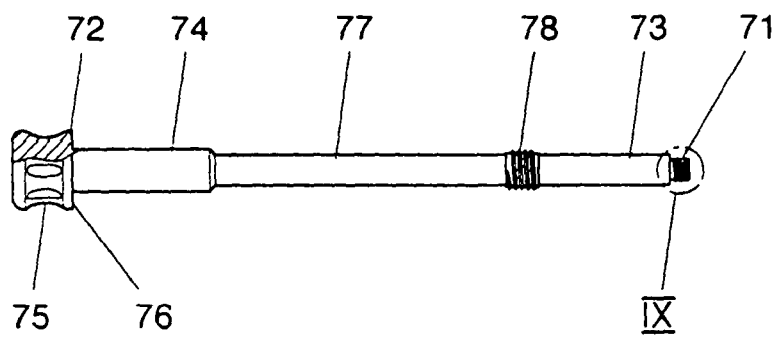
FIG. 8 is a sectional side view of the inner bar of FIG. 7.

FIG. 7 shows a perspective view of the preferred inner bar 70 of the extractor device 50 according to FIG. 4. FIG. 8 shows a sectional side view of the inner bar 70 of FIG. 7. The inner bar 70 comprises a first distal bar portion 74 having an outer diameter similar to the first inner diameter of the hollow sleeve 60 so that the bar 70 can be inserted with little play into the hollow sleeve 60 from the side of the opening 67. The distal bar portion 74 ends in an abutment flange 76 of the gripping depression 75. On the opposite end of the distal bar portion 74 a middle bar portion 77 has a thinner cylindrical portion. The middle bar portion 77 is followed by a threaded portion 78 having a longitudinal length which is preferably identical to the inner threaded portion 68 of the outer sleeve 60. The location of thread 78 also depends on the location of the inner threaded portion 68. If portion 68 is located near or under the first handle part 62 then the threaded portion 78 of the inner bar 70 is located near or in the area of the distal bar portion 74.

Figure 9:
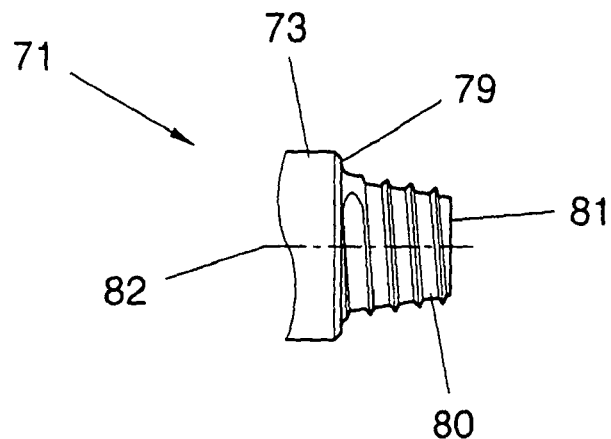
FIG. 9 is an enlarged view of the tip of the inner bar of FIG. 7.

In the embodiment shown in the drawings, the threaded portion 78 is proximally followed by the proximal inner bar section 73. Inner bar section 73 is followed by a tip portion 71 of the inner bar 70, which is shown in FIG. 9 in an enlarged view.

The tip portion 71 preferably comprises four full threads of a thread 80 ending in a flat surface 81. In the preferred embodiment the thread 80 is conical and is connected with the inner bar section 73 via a chamfered flange 79. The direction of the threading 80 is identical to the direction of the thread 78. The main axis 82 of the bar 70 coincides with the axis 82 of the thread 80 and with the longitudinal main axis 82a of the sleeve 60. The advantage of a conical thread 80 is the easier fixation of the bar onto inserts 10 with damaged threads 12.

The function of the device 50 is as follows. The device is assembled through insertion of the bar 70 into the hollow sleeve 60 through the distal opening 67 within the sleeve 60 such that axis 82, 82a and coaxial. The thread 78 of the bar 70 engages the inner thread 68 of the hollow sleeve 60 and is rotated until the tip 71 is extending beyond the end of the hollow shaft 60 or until the threads 68 and 78 come free one from the other. Both threads 68 and 79 are right-handed, i.e. the thread 78 advances when turned clockwise with respect to its mating part 68. The flange 76 of the second handle part 72 can ultimately abut against the first handle part 62 of the hollow sleeve 60. The thread 78 may then no longer be in engagement with thread 68.

The bar 70 is then screwed into the insert 10 by turning the handle 72, i.e. the conical thread 80 is engaging the internal threading 12 of the insert 10. Preferably the abutment flange 79 of the tip is coming into contact with the upper surface 21 of the insert 10. Then the abutment ring 64 is advanced to come into contact with the surface 8 of the plate 1 beside the insert 10, i.e. the abutment ring 64 does not contact surface 21 but touches the plate 1 outside the circumference 21 of the insert 10. This contact is possible independent from the angle and direction of the insert bore 11 as discussed above. The relative advancement of sleeve 60 in relation to the bar 70 can be a longitudinal movement or comprising a rotation when the threads 68 and 78 come into engagement. For a rotational movement the handle part 62 is rotated against the handle part 72 of the inner bar, which is maintained in its position. The internal thread 12 of the insert 10 is also right-handed.

When the abutment ring 64 comes in contact with the upper surface 8 of the plate 1 (and not with the insert 10), then the extractor sleeve 60 is further rotated in the direction opposite to the above mentioned rotation of the bar 70. This rotation retracts the rod 73 further into the sleeve 60 and therefore exerts a force in the longitudinal direction of axis 82 of the extractor device 50 on the insert 10 against the plate 1. This leads to the situation that engagement means 25 of the insert 10 are overcome and the insert 10 will be extracted. The advantage of right-handed threads 68 and 78 resides in the fact that the rotation to extract the insert 10 additionally blocks the thread 12 of the insert 10 in thread 80 of the tip 71.

In another embodiment (not shown) the threads 68 and 78 may be left-handed. Then the surgeon has the usual anti-clockwise movement to extract the insert; however, it is then possible that the thread 12 of the insert 10 becomes no longer fastened to the conical thread 80 of the inner bar 70.

It is clear that the abutment ring 64 can be of a different form than having a circular shape. It may have a polygonal abutment surface or the plane of the abutment surface can comprise an angle with the plane perpendicular to the longitudinal direction of axis 82 of the bar 70.

Figure 10:
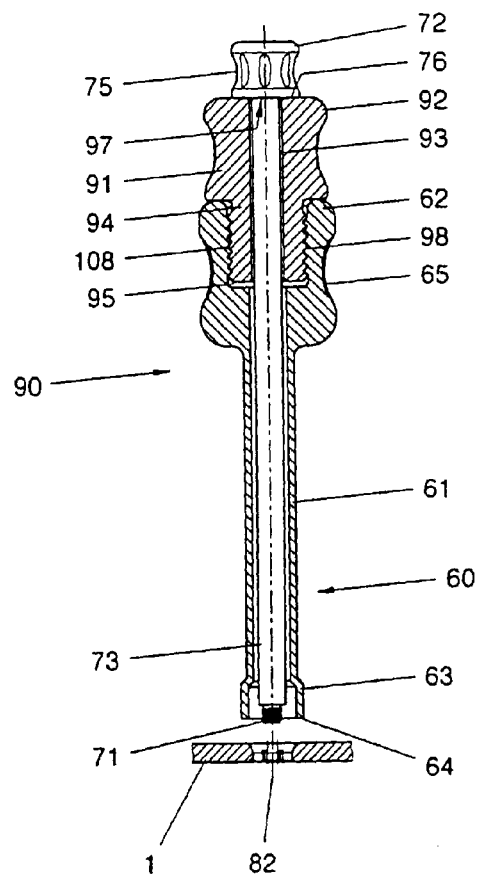
FIG. 10 is a sectional side view of an extractor device according to a second embodiment of the invention in vicinity of an load-bearing element.

FIG. 10 shows a sectional side view of an extractor device 90 according to a second embodiment of the invention in vicinity of an load-bearing element 1. Extractor device 90 comprises three different parts, an outer sleeve 60 and an inner bar 70 extending on both sides beyond the through going bore inside the sleeve 60. Additionally there is an intermediate element 91 essential to the function of the device.

The outer sleeve 60 comprises a hollow sleeve part 61 having a first handle part 62 being an integral part of the sleeve 60. The first handle part 62 comprises a circumferential depression 65 to provide a grip portion for the hand of a user of the device 50. A thickened abutment sleeve 63 is provided on the opposite end of the hollow sleeve part 61 ending in a round abutment ring 64 having a larger diameter than the diameter of the proximal bar section 73 of the inner bar 70. The function of the abutment ring 64 is identical as explained above.

The inner bar 70 extends on both sides of outer sleeve 60. On the side of the first handle part 62 the inner bar 70 comprises a second handle part 72 having a circumferential gripping depression 75. Between the two handle parts 62 and 72 the intermediate element 91 is introduced.

The intermediate element 91 has a through bore 93 for the inner bar 70. The intermediate element 91 comprises a grip portion 92 being able to be in abutment against the handle part 72 of inner bar 70 on one side and with the handle part 62 of the sleeve 60 on the other side. On the side of the handle part 72 the intermediate element 91 comprises an opening 97 in the flat upper surface to receive the inner bar 70. On the side of the handle part 62 the intermediate element 91 comprises a smaller central projection 94 with an external thread 98.

Sleeve 60 incorporates in the handle part 62 a recess 95 to accommodate the projection 94, wherein the recess 95 comprises an internal thread 108.

As in the first embodiment of an extractor device 50, an engagement thread 71 is provided at the leading end of the proximal bar section 73 extending beyond the hollow sleeve 60.

Inner bar 70 of the extractor device 90 comprises a bar portion 74 having an outer diameter similar to the inner diameter of the hollow sleeve 60 and similar to the inner diameter of the intermediate element 91 so that the bar 70 can be inserted with little play into the intermediate element 91 and into the hollow sleeve 60 from the side of the openings 67 and 97. The bar portion 74 ends in an abutment flange 76 of the gripping depression 75.

The tip portion 71 of extractor device 90 can be the same as the tip portion 71 of extractor device 50.

The function of the device 90 is as follows. The device is assembled through insertion of the intermediate element 91 into the hollow sleeve 60 through the opening 67 within the sleeve 60. The thread 98 of the intermediate element 91 engages the inner thread 108 of the hollow sleeve 60 and is rotated until the handle part 92 abuts against the handle part 62 or the projection 94 reaches the depth of the recess 95. Both threads 98 and 108 are right-handed. The bar 70 is then entered into intermediate element 91 and hollow sleeve 60 and screwed into the insert 10 by turning the handle 72, i.e. the conical thread 80 is engaging the internal threading 12 of the insert 10. Then the abutment ring 64 is advanced to come into contact with the surface 8 of the plate 1 beside the insert 10, i.e. the abutment ring 64 does not contact surface 21 but touches the plate 1 outside the circumference 21 of the insert 10.

The handle part 92 of the intermediate element 91 is rotated against the handle part 62 of the hollow sleeve 60, which is maintained in its position. As rotation occurs, the intermediate element 91 and the hollow sleeve 60 move apart, while the inner bar 70 just follows, because the handle part 72 is in abutment with the intermediate element 91. The rotation of intermediate element 91 indirectly retracts the rod 73 further into the sleeve 60 and therefore exerts a force in the longitudinal direction of said axis 82 of the extractor device 90 on the insert 10 against the plate 1. This leads to the situation that engagement means 25 of the insert 10 are overcome and the insert 10 will be extracted. In the case of the second embodiment it is advantageous to use right-handed threads 80 and 12 whereas threads 98 and 108 are left-handed. Then the rotation to extract the insert 10 blocks the insert 10 in thread 80 of tip 71.

However in all embodiments it is possible to switch the handedness of any pair of threads.

Upon extraction of an insert 10, the insert 10 either completely or nearly disappears within the hollow thickened abutment sleeve 63.

Figure 11:
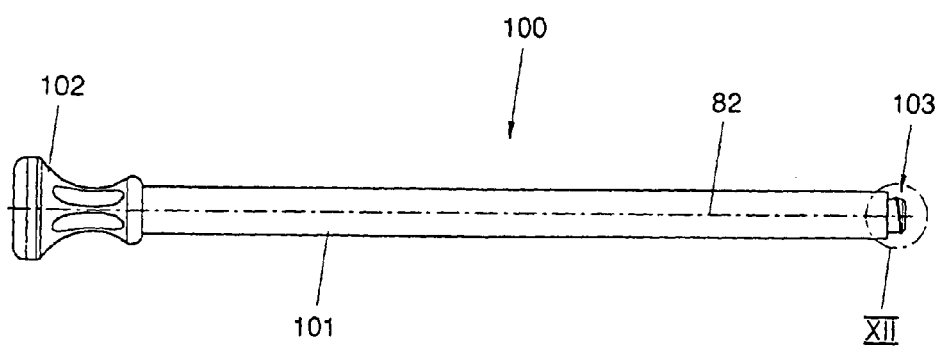
FIG. 11 is a side view of an insertion device according to an embodiment of the invention.
Figure 12:
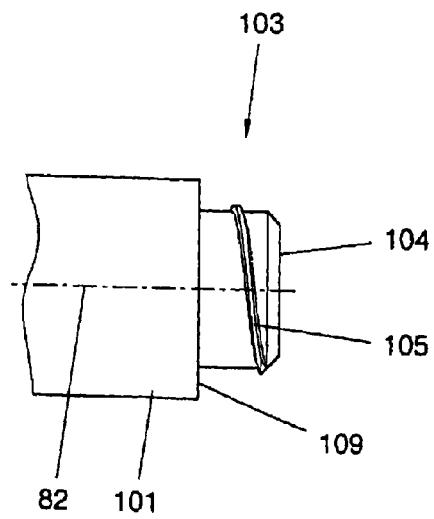
FIG. 12 is an detail of the tip of the insertion device according to FIG. 11.

FIG. 11 shows a side view of an insertion device 100 according to an embodiment of the invention and FIG. 12 is an detail of the tip of the insertion device 100 according to FIG. 11. Insertion device 100 is very similar to inner bar 70, having a bar 101 with a handle part 102 at one end, whereas the other free end of the bar 101 comprises a cylindrical tip 103 with a smaller diameter than the bar 102. Said tip 103 comprises one single thread 105 and ends with a flat bottom surface 104, which can be chamfered for easier insertion. Tip 103 is positioned within the opening of an insert 10 and the thread 105 engages the complementary thread 12 of the insert 10. It is clear that due to the shortness of the tip 103 the resilient extensions 25 of insert 10 are not in the vicinity of the tip 103 but spaced apart in the longitudinal direction of axis 82b of the insertion device 100. It is possible that the distance between the thread 12 and the upper surface 21 of the insert 10 is such that surface 21 can abut against the abutment flange 109 of the bar 101.

Initially the insert 10, 20 to be inserted into a plate 1 is affixed to the insertion device 100 as mentioned above. Then the device 100 with the insert 10, 20 at its tip is pushed against and into the plate 1 until the locking extensions 25 of the insert 10, 20 are pushed beyond the smallest waist part, i.e. the smallest diameter in the hole 2 of a plate 1. Then the insertion device 100 can be rotated in the opposite direction to free the insert 10, 20 from its tip. This can be done directly, because the inserts 10, 20 are oblong.

FIG. 13 shows a perspective view of a second insert 110 to be used with a load-bearing element 1. FIG. 14 is a sectional side view of the insert 110 according to FIG. 13 and FIG. 15 is an enlarged side view showing a detail of the resilient extension 25a of the insert according to FIG. 13. Insert 110 comprises a flat upper surface 121 at its circumference wherein on the inside of surface 121 a step-like recess 122 is provided. The resilient extension 25a on each side is separated as within the embodiment according to FIG. 1 from the semicircular extensions 24a by two slots 26a. The resilient extension 25a comprises a special triangular form when seen from the side or in a cross section.

On the inside the resilient extension 25a comprises the inner thread 12 which can be oriented in different ways and angles. On the outside the insert 110 has a waist 129, i.e. an area with minimum exterior diameter. Towards the upper side 121 of the insert 110 there is the larger spherical surface 23a or another complementary surface for the bore 2 in plate 1. Towards the bottom side there is provided, on the resilient extensions 25a, a thickened region 127. In the embodiment shown the thickened region 127 has a thickest part near the lower end of the extension 25a, i.e. the cross section through the extension 25a always shows a triangle form. Advantageously the form of the plate 1 is complementary, i.e. the plate has at least on its sides a recess to accommodate the thickened region 127. The chamfered lower end 128 facilitates the introduction of the insert 110 into a plate 1. The angle of the surface 128 in relation to the bottom surface is 120 degree (reference numeral 124). The triangle form 127 also facilitates the extraction of the insert 110 because the inclined surface 126, e.g. with an angle of 30 degree to the vertical axis of the insert 110, can slide on the complementary inclined surface of the plate 1 or on the smallest internal diameter of hole 2 thereof.

Although the described drawings already show a whole series of possible configurations of the invention, the invention is and should be limited only by the parameters of the attached claims.

The advantage of the invention is that it offers the surgeon using a plate 1 with conventional standard bores 2 and inserted inserts 10, 110 the possibility of adapting the plurality of angularly-stable mono-axial bores by replacement of inserts, and furthermore, that this is made possible intraoperatively.

The invention claimed is:

1. A method for extracting an insert from an opening in a bone plate comprising:

providing an elongated bone plate having a bone contacting surface and having at least one elongate opening for receiving a bone screw, said opening having a recessed outwardly facing surface around the opening, said recessed outwardly facing surface tapering towards the bone contacting surface from a first to a second smaller cross-section;

providing an elongate insert mounted in the elongate opening wherein the insert exhibits a continuous external portion that is generally complementary to the recessed outwardly facing surface and an extension portion complimentary to an internal surface of the opening extending from the second smaller cross-section toward the bone contacting surface and wherein the insert exhibits a threaded central through-bore for mounting the body of the bone screw wherein the extension portion has at least one deflectable portion that extends along an elongate side of the insert internal portion;

threading an extractor into the threaded central through bore of the elongate insert, the extractor having an outer hollow sleeve, the hollow sleeve comprising an introduction opening at a first end and a proximal abutment surface at a second end engagable with a surface portion of the load-bearing element around the insert, the hollow sleeve further comprising an inner threaded portion between said introduction opening and said abutment surface and an inner bar, the bar having a diameter enabling the insertion of the bar into said distal introduction opening of the hollow sleeve and comprising a threaded end portion for engaging the threaded bore of the elongate insert to be extracted and an outer thread on an intermediate portion wherein the outer threaded portion is arranged to engage said inner threaded portion of the hollow sleeve;

positioning the outer threaded portion of said inner bar being at a longitudinal distance from the insert engaging threaded end portion thereof to enable that threaded portion to extend beyond the proximal abutment surface;

threading the end portion into the central bore of the insert and limiting the engagement of the thread on the first end of the bar with the thread on the insert bore to less than an entire length of the threaded bore to allow the deflectable insert portion to deflect inwardly; and removing the insert by pulling on the extractor thereby allowing the deflection of the internal portion.

2. The method as set forth in claim 1, wherein the insert engaging threaded portion of the bar has a conical thread.

3. The method device as set forth in claim 1, wherein an abutment flange connects insert engaging threaded portion with a larger bar section of said inner bar.

4. The method device as set forth in claim 1, wherein the inner bar comprises at a first end a handle part having an abutment flange.

5. The method device as set forth in claim 1, wherein the hollow sleeve comprises at its second end an enlarged abutment section to engage a surface of the load-bearing element.

6. The method device as set forth in claim 5, wherein the hollow sleeve comprises at its first end a hollow handle part.

7. The method device as set forth in claim 1, wherein the threads of sleeve and bar, respectively, are located in the first third of the device between the abutment surface of said first end of said outer sleeve.

8. The method device as set forth in claim 1, wherein the threads of sleeve and bar or intermediate element have the same handedness as the thread of the tip of the inner bar.

9. The method device as set forth in claim 1, wherein the abutment surface is a cylindrical ring, an elliptical ring or a polygonal strip.

10. A method for extracting an insert with an internally threaded bore therethrough from an opening in a bone connection element usable within an implantable orthopedic device, such as a bone plate:

providing an elongated load-bearing element having a bone contacting surface and having at least one elongate opening for receiving a bone screw, said opening having a recessed outwardly facing surface around the opening, said recessed outwardly facing surface tapering towards the bone contacting surface from a first to a second smaller cross-section;

providing an elongate insert mounted in the elongate opening wherein the insert exhibits a continuous external portion that is generally complementary to the recessed outwardly facing surface and complimentary to an internal surface of the opening extending from the second smaller cross-section toward the bone contacting surface and wherein the insert exhibits a threaded central through-bore for mounting the body of the bone screw wherein the insert has at least one deflectable internal portion section that extends along an elongate side of the insert internal portion;

inserting a bar with a threaded first end and an outer threading into a hollow sleeve having an internal threading for engaging the outer threading of the bar and an abutment tip for engaging the bone plate;

screwing the first end of the bar into the internal threaded central bore of the insert to be extracted, advancing the abutment tip of the hollow sleeve into contact with a surface of the bone connection element, wherein the relative advancement of the hollow sleeve relative to the bar is a longitudinal movement resulting from rotating the engaged inner and outer threads of sleeve and bar; and extracting the insert through further rotation of sleeve or an intermediate element located between the sleeve and the bar, wherein the inner bar or the sleeve, respectively, are maintained in its rotational position, said rotation retracting the bar into the hollow sleeve and exerting a force in a longitudinal direction of the sleeve and bar on the insert against forces holding the insert within the opening in the bone connection element and extracting the insert and means for limiting the engagement of the thread on the first end of the bar with the thread on the insert bore to less than an entire length of the threaded bore to allow the inward deflection of the deflectable internal section of the insert.

11. The method as set forth in claim 10, wherein the extractor device is assembled by inserting the inner bar into the hollow sleeve from an opening at a first end of the hollow sleeve and relative rotation of the hollow sleeve and bar to engage their inner and outer threads, respectively, until the tip of the bar extends beyond a second end of the hollow sleeve.

12. The method of claim 11 wherein the first end of said tubular sleeve includes an abutment portion.

13. The method of claim 12 wherein said second end of said tubular sleeve has a handle part for rotating said sleeve.

14. The method of claim 13 wherein said second end of said bar has a handle part for rotating said bar.

* * * * *